(12) United States Patent
Bara

(10) Patent No.: US 6,251,375 B1
(45) Date of Patent: Jun. 26, 2001

(54) USE OF A VOLATILE POLYFLUORINATED SOLVENT AS A DRYING ACCELERATOR IN COSMETIC PRODUCTS

(75) Inventor: Isabelle Bara, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/220,797

(22) Filed: Dec. 28, 1998

(30) Foreign Application Priority Data

Dec. 29, 1997 (FR) .................................................... 97 16628
Jun. 30, 1998 (FR) .................................................... 98 08338

(51) Int. Cl.[7] ............................. A61K 7/04; A61K 7/025; A61K 7/021; A61K 7/035; A61K 7/06
(52) U.S. Cl. ................................. 424/61; 424/64; 424/69; 424/70.7; 424/63; 424/401; 424/59
(58) Field of Search ............................... 424/401, 59, 61, 424/63, 69; 514/747, 759, 845, 938

(56) References Cited

U.S. PATENT DOCUMENTS 5,843,412 * 12/1998 de La Poterie et al. .
5,851,539 * 12/1998 Mellul et al. ........................ 424/401

FOREIGN PATENT DOCUMENTS 0 595 683 A1  5/1994  (EP) .
2 593 392     7/1987  (FR) .
2 756 176     5/1998  (FR) .

OTHER PUBLICATIONS

Chemical Abstracts 117:137 461 & JP 04 139 121 A, May 13, 1992.

Chemical Abstracts 110:160 222 & JP 63 002 916 A, Jan. 7, 1988.

* cited by examiner

Primary Examiner—Diana Dudash
Assistant Examiner—Alysia Berman
(74) Attorney, Agent, or Firm—Nixon & Vanderhye P.C.

(57) ABSTRACT

The present invention provides the process for accelerating the drying time of a cosmetic makeup, sun protection or nail care compositions which includes introducing at least one volatile organic polyhalogenic solvent into the composition.

7 Claims, No Drawings

USE OF A VOLATILE POLYFLUORINATED SOLVENT AS A DRYING ACCELERATOR IN COSMETIC PRODUCTS

The present invention relates to the use of a certain class of volatile organic polyhalogen compounds, in which the halogen atom is fluorine, in cosmetic compositions for makeup, sun protection or nailcare, in order to accelerate their drying time.

The problem associated with the drying of cosmetic products following their application is of great importance for users.

In fact, a product which has a slow drying rate is generally not very well accepted, whether it be a foundation, a lipstick or a nailcare product.

Moreover, the rate of drying must not be too rapid, since in that case it would be liable to produce unattractive shrinkage phenomena.

Although various studies have been carried out with a view to improving the drying time of cosmetic compositions, especially makeup compositions, no satisfactory solution has been proposed.

Following numerous studies on various types of compound it has surprisingly and unexpectedly been found that by using a certain class of volatile organic polyhalogen solvents in which the halogen atom is fluorine it was possible to bring about in a particularly satisfactory and effective manner an improvement in the drying time of cosmetic compositions.

In fact, the use of these solvents, referred to below as volatile polyfluorinated solvents has been found to enable particularly rapid drying to be obtained following application of the composition to the skin, which is not the case with the prior art compositions.

Another particularly important advantage is to be able to obtain the compositions in perfect safety in so far as the volatile polyfluorinated solvents do not have a flash point, which makes it possible to prepare compositions at high temperature and therefore has a certain advantage when the melting point of the substances used is greater than room temperature.

Finally, the use of volatile polyfluorinated solvents facilitates the incorporation into compositions of high concentrations of non-volatile fluorinated derivatives, the latter being completely miscible with the volatile polyfluorinated solvents. Hence it is possible to obtain a residual film which is highly fluorinated, has a glossy or satin finish, and is resistant to water and fatty substances.

The present invention therefore provides for the use in a cosmetic makeup, sun protection or nailcare composition of at least one organic polyhalogen solvent as a drying accelerator, the halogen atom being fluorine and the said solvent having a vapour pressure of more than 20 mbar (2000 Pa) at 25° C. and preferably more than 40 m bar (4000 Pa).

Among the volatile polyfluorinated solvents which can be used as drying accelerators and which meet the above-mentioned vapour pressure criterion mention may be made in particular of:

1) perfluorocycloalkyl compounds of the formula (I):

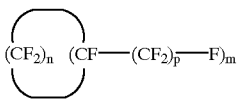

(I)

in which
n is 3, 4, or 5
m is 1 or 2, and
p is 1, 2 or 3
with the proviso that when m=2 the groups are not necessarily in the alpha position with respect to one another, 2) fluoroalkyl or heterofluoroalkyl compounds of the formula (II):

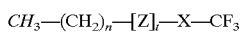

(II)

in which:
t is 0 or 1,
n is 0, 1, 2 or 3,
X is a linear or branched divalent perfluoroalkyl radical having 2 to 5 carbon atoms, and
Z represents O, S or NR, where R is hydrogen or a radical $-(CH_2)_n-CH_3$ or $-(CF_2)_m-CF_3$, where m is 2, 3, 4 or 5, 3) perfluoroalkane compounds of the formula (III):

(III)

in which:
n is from 2 to 6, and 4) perfluoromorpholine derivatives of the formula (IV):

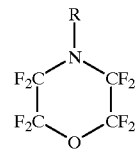

(IV)

in which:
R is a $C_1$–$C_4$ perfluoroalkyl radical.

Among the perfluorocycloalkyls of formula (I) mention may be made in particular of perfluoromethylcyclopentane and perfluorodimethylcyclohexane, which are sold, respectively, under the names FLUTEC PC1® and FLUTEC PC3® by the company BNFL FLUOROCHEMICALS Ltd., and perfluorodimethylcyclobutane.

Among the fluoroalkyl or heterofluoroalkyl compounds of formula (II) mention may be made in particular of methoxynonafluorobutane, which is sold under the name HFE-7100® by the 3M Company, or ethoxynonafluorobutane, which is sold under the name HFE-7200® by the company ARCHIMEX.

Among the perfluoroalkane compounds of formula (III) mention may be made in particular of dodecafluoropentane and tetradecafluorohexane.

Among the perfluoromorpholine derivatives of formula (IV) mention may be made in particular of 4-trifluoromethylperfluoromorpholine and 4-pentafluoroethylperfluoromorpholine.

The volatile polyfluorinated solvents as defined above must also meet the criterion of the boiling point, which must be between 20 and 75° C. and preferably between 25 and 65° C.

Within the compositions according to the invention the proportion of volatile polyfluorinated solvent is generally between 2 and 98% by weight but preferably between 5 and 70% by weight relative to the total weight of the composition.

According to one preferred embodiment of the invention the compositions comprise particles of pigment and/or of dye and/or of filler.

The pigments of the compositions according to the invention, and the dyes and fillers, are in the form of very fine particles having an average particle size of between approximately 0.02 and 50 $\mu$m.

The pigments of the compositions may be inorganic or organic or else may be in the form of metal lakes. Among these pigments mention may be made of titanium dioxide, zinc oxide, D&C Red No. 36 and D&C Orange No. 17, calcium lakes of D&C Red No. 7, 11, 31 and 34, barium lake of D&C Red No. 12, D&C Red No. 13 strontium lake, aluminium lakes of FD&C Yellow No. 5, of FD&C Yellow No. 6, of D&C Red No. 27, of D&C Red No. 21 and of FD&C Blue No. 1, iron oxides, manganese violet, chromium oxide and ultramarine blue.

The fillers may be of natural or synthetic origin. Among these mention may be made in particular of:
a) mineral powders such as talc, kaolin, mica, silica, silicates, alumina, zeolites, hydroxyapatite, sericite, titanium micas, barium sulphate, bismuth oxychloride, boron nitride and metal powders such as aluminium powder;
b) vegetable powders, such as starch, maize, wheat or rice powders;
c) organic powders, such as nylon, polyamide, polyester, polytetrafluoroethylene or polyethylene powders.

Moreover, these various powders may be coated, for example with metal salts of fatty acids, amino acids, lecithin, collagen, silicone compounds, fluorinated compounds, or with any other customary coating.

Among the dyes mention may be made of eosine derivatives, such as D&C Red No. 21, and halogenated fluorescein derivatives, such as D&C Red No. 27, D&C Orange No. 5 in combination with D&C No. 21 and D&C Orange No. 10.

Depending on the compositions, the dyes may be in particle form or may be in a form in which they are solubilized in the vehicle of the composition.

Within the compositions according to the invention the proportion of at least one pigment and/or dye is generally between approximately 0.1 and 15% by weight relative to the total weight of the composition.

The fillers may generally be present in a maximum proportion of approximately 98% by weight relative to the total weight of the composition.

According a first particular embodiment of the compositions according to the invention, the latter are anhydrous and comprise a fatty phase in a proportion of between approximately 0.3 and 90% by weight relative to the total weight of the composition.

The fatty phase generally consists of one or more fatty substances, which may be selected from oils, waxes, gums and/or so-called pastelike fatty substances.

A—The oils of the fatty phase may be mineral, animal, vegetable or synthetic in origin, and these may be volatile or non-volatile at ambient temperature.

As oils of mineral origin mention may be made in particular of liquid paraffin and liquid petroleum.

As oils of animal origin mention may be made in particular of squalane or perhydrosqualene.

As oils of vegetable origin mention may be made in particular of sweet almond oil, calophyllum oil, palm oil, avocado oil, jojoba oil, sesame oil, olive oil, castor oil, and cereal germ oils such as, for example, wheat germ oil.

As synthetic oils mention may be made in particular of:
(1) esters of the formula (III):

$$R_1\text{—COOR}_2 \quad (III)$$

in which:
$R_1$ is the residue of a higher fatty acid having 7 to 20 carbon atoms and
$R_2$ is a hydrocarbon radical having 3 to 30 carbon atoms.

Among these esters mention may be made in particular of purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, isononyl isononanoate, and esters derived from lanolic acid, such as isopropyl lanolate and isocetyl lanolate.

As other synthetic oils mention may be made, moreover, of isoparaffins, isododecane, isohexadecane, polyisobutenes and hydrogenated polyisobutene, and also acetylglycerides, and octanoates and decanoates of polyalcohols such as those of glycol and of glycerol, the ricinoleates of alcohols and of polyalcohols such as that of cetyl alcohol, propylene glycol dicaprylate and diisopropyl adipate;
(2) fatty alcohols such as oleyl alcohol, linoleyl alcohol, linolenyl alcohol, isostearyl alcohol and octyldodecanol;
(3) silicone oils, such as optionally functionalized linear polydiorganosiloxanes, cyclic polydiorganosiloxanes and, in particular, cyclotetradimethicones and cyclopentadimethicones, and organopolysiloxanes such as alkyl-, alkoxy- or phenyldimethicones, and especially phenyltrimethicone;
(4) non-volatile fluorinated oils, such as perfluorodecalin, perfluorophenanthrene, perfluoroalkanes and perfluoropolyesters, and partially fluorinated hydrocarbon oils.

According to one particularly preferred form of the invention use is made of non-volatile perfluoropolyethers of the formulae (IV) and (V):

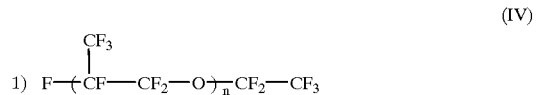

in which:
n=7 to 30,

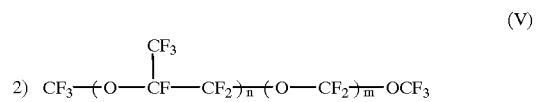

in which
n and m=20 to 40.

Among these compounds mention may be made of those sold under the names FOMBLIN C® and GALDEN® by the company ASSIMONT, or else under the name FLUORTRESS LM 36® by the company DU PONT.

B—The waxes of the fatty phase may be mineral, fossil, animal, vegetable or synthetic in origin or else may be hydrogenated oils or fatty esters which are solid at 25° C.

Among mineral waxes mention may be made in particular of microcrystalline waxes, paraffin, petroleum jelly and ceresine.

Among fossil waxes mention may be made of ozokerite and montan wax.

Among the waxes of animal origin mention may be made of beeswax, spermaceti, lanolin wax, and derivatives obtained from lanolin, such as lanolin alcohols, hydrogenated lanolin, hydroxylated lanolin, acetylated lanolin, fatty acids of lanolin, and acetylated lanolin alcohol.

Among the waxes of vegetable origin mention may be made in particular of candelilla wax, carnauba wax, Japan wax and cocoa butter.

Among synthetic waxes mention may be made in particular of ethylene homopolymers and of the copolymers of ethylene with a monomer of the formula (VI):

$$CH_2=CH-R_3 \qquad (VI)$$

in which:

$R_3$ is an alkyl radical having 1 to 30 carbon atoms, or an aryl or aralkyl radical.

The alkyl radical having 1 to 30 carbon atoms is preferably the methyl, ethyl, propyl, isopropyl, butyl, decyl, dodecyl or octadecyl radical.

It is also possible to use waxes obtained by Fischer-Tropsch synthesis, as well as silicone waxes.

Among the hydrogenated oils which are solid at 25° C. mention may be made in particular of hydrogenated castor oil, hydrogenated palm oil, hydrogenated tallow and hydrogenated coconut oil.

Among the fatty esters which are solid at 25° C. mention may be made in particular of propylene glycol monomyristate and myristyl myristate.

As waxes which can be use din the compositions according to the invention mention may also be made of cetyl alcohol, stearly alcohol, mono-, di- and triglycerides which are solid at 25° C., stearic monoethanolamide, rosin and its derivatives such as the abietates of glycol and of glycerol, sucroglycerides, and the oleates, jyristates, lanolates, stearates and dihydroxystearates of calcium, of magnesium, of zinc and of aluminium.

C—The fatty substances of pastelike type may be mineral, animal, vegetable or synthetic in origin.

Among the pastelike fatty substances mention may be made in particular of synthetic esters such as arachidyl propionate, vinyl polylaurate, polyethylene waxes, and organopolysiloxanes such as alkyldimethicones, alkydimethicones or dimethicone esters.

The anhydrous compositions as defined above may of course additionally include one or more conventional cosmetic or dermatological additives or adjuvants.

These anhydrous compositions are generally makeup products or sun protection products and are present, for example, in the form of an oily gel, a solid product such as a compacted or cast powder, or else a stick such as a lipstick, for example.

When the compositions are in the form of an oily gel they generally comprise an oily gelling agent in addition to the above-described constituents.

Among the oily gelling agents mention may be made in particular of metal esters, such as polyoxyaluminium stearate and magnesium or aluminium hydroxystearate, esters of fatty acids and glycol, triglycerides, mixtures of fatty alcohols, cholesterol derivatives, and especially hydroxychloresterol, and clay minerals which swell in the presence of oil, especially those belonging to the group of the montmorillonites.

The oily gelling agents may be present in a proportion which is highly variable depending on the desired texture of the compositions. In the majority of cases, however, they are present in a proportion of between approximately 0.1 and 30% by weight relative to the total weight of the composition.

Among the makeup products which are produced from these anhydrous compositions mention may be made of foundations, mascaras, eyeliners, lipsticks, eyeshadows and rouges.

These anhydrous compositions may also be present in the form of liquid oily products for nailcare, the fatty phase comprising at least one active agent.

Among the active agents of these nailcare compositions mention may be made in particular of ceramides, phytantriol, D-panthenol, α-hydroxy acids, UV screens, vitamins, keratin and biotin.

According to a second embodiment of the compositions according to the invention, the latter are dispersions in the form of a stable water-in-oil (W/O) or oil-in-water (O/W) emulsion which consist essentially (i) of a fatty phase in a proportion of between approximately 0.1 and 50% by weight relative to the total weight of the composition, it being possible for the said fatty phase to comprise at least one fatty substance as defined above in a proportion of between approximately 0.1 and 95% by weight relative to the total weight of the composition, (ii) of an aqueous phase in a proportion of between approximately 4 and 97% by weight relative to the total weight of the composition, and (iii) of at least one emulsifier in a proportion of between approximately 1 and 10% by weight relative to the total weight of the composition in emulsion form.

As an emulsifier or surfactant which can be used in the compositions in the form of a W/O or O/W emulsion, mention may be made in particular of silicone surfactants, and especially those belonging to the class of the alkyl- or alkoxydimethicone copolyols. Among the alkyl- or alkoxydimethicone copolyols mention may be made in particular of the compounds of the following general formula:

$$CH_3-\underset{\underset{CH_3}{|}}{\overset{\overset{CH_3}{|}}{Si}}O-\left[\underset{\underset{CH_3}{|}}{\overset{\overset{CH_3}{|}}{Si}}O\right]_u-\left[\underset{\underset{(CH_2)_3}{|}}{\overset{\overset{CH_3}{|}}{Si}}O\underset{\underset{O-(C_2H_4O)_x-(C_3H_6O)_y-R}{|}}{}\right]_v-\left[\underset{\underset{R'}{|}}{\overset{\overset{CH_3}{|}}{Si}}O\right]_w-\underset{\underset{CH_3}{|}}{\overset{\overset{CH_3}{|}}{Si}}-CH_3 \qquad (VII)$$

in which:

R is a hydrogen atom, a $C_1$–$C_{16}$ alkyl, or an alkoxy or acyl,

R' is a $C_8$–$C_{22}$ alkyl or alkoxy radical, u=0 to 200, v=1 to 40, w=1 to 100, the molecular weight of the radical —O—$(C_2H_4O)_x$—$(C_3H_6O)_y$—R being from 250 to 2000, where x and y are chosen such that the ratio by weight of the oxyethylene/oxypropylene groups is between 100:0 and 20:80.

Among the commercial products which may contain, as a whole or in part, alkyldimethicone copolyols, mention may be made in particular of those sold under the names ABIL WE09®, ABIL EM90® or ABIL WS08® by the company GOLDSCHMIDT, Q2 5200® or Q2 3225C® by the company DOW CORNING, and 218 1138® by the General Electric Company.

The surfactants may also be selected from anionic or nonionic surfactants. In this regard reference may be made to the document Encyclopedia of Chemical Technology, KIRK-OTHMER, volume 22, pages 333–432, 3rd edition, 1979, WILEY, for the definition of the properties and functions (emulsifying) of surfactants, especially pages 347–377 of this reference, for nonionic and anionic surfactants.

The surfactants from these two groups that are preferably used in the compositions according to the invention are:
  among the nonionic surfactants: fatty acids, fatty alcohols, polyethoxylated or polyglycerolated fatty alcohols, such as polyethoxylated stearly alcohol or polyethoxylated cetylstearyl alcohol, esters of fatty acids and sucrose, alkylglucose esters, especially polyoxyethylenated $C_1$–$C_6$-alkylglucose fatty esters, and
  among the anionic surfactants: amine stearates.

These emulsions are preferably in the form of creams and can be used as makeup products or suncare products. In the latter case they comprise UVA and/or UVB sunscreens and also white pigments, in a proportion which is variable depending on the desired protection factor.

The compositions such as those described above, whether of anhydrous type or in the form of a dispersion, exhibit excellent cosmetic properties, such as, in particular, excellent ease of application and great softness, and lead to the production of a homogeneous makeup.

The compositions as above described may additionally comprise one or more conventional cosmetic adjuvants, such as vitamins, hormones, antioxidants, rheological agents, preservatives, perfumes, thickeners, hydrating agents, humectanta, anionic, nonionic or amphoteric polymers, or cosmetic or dermatological active substances.

The present invention also provides the process for preparing a cosmetic makeup, sun protection or nailcare composition in order to accelerate its drying time, this process consisting in introducing into the said composition an effective quantity of at least one volatile polyfluorinated solvent as defined above having a vapour pressure of more than 20 mbar (2000 Pa) at 25° C.

The invention will now be illustrated by the various examples given below, in which the quantities are by weight.

EXAMPLES

Example 1: Lipstick

| | |
|---|---|
| Methoxynonafluorobutane (HFE-7100) | 10 g |
| Perfluorodecalin | 35 g |
| Wax | 40 g |
| Polyperfluoroisopropyl ether (FLUORTRESS LM 36 ®) | 5 g |
| Pigments | 10 g |

The fatty substances are mixed while hot but at a temperature lower than that at which the volatile oil evaporates, the pigments are introduced with stirring, and the melted mixture is subsequently poured into lipstick moulds.

After cooling and removal from the moulds, lipsticks are obtained which have a good texture, are easy to apply and have a very short drying time.

In this example the methoxynonafluorobutane can be replaced by an equivalent amount of tetradecafluorohexane or perfluorodimethylcyclohexane.

Example 2: Foundation

| | |
|---|---|
| Perfluoromethylcyclopentane (FLUTEC PC 1 ®) | 20 g |
| Alkyldimethicone copolyol; (ABIL WE 09 ®) | 5 g |
| Cyclomethicone | 10 g |
| Pigments | 7 g |
| Water | q.s. 100 g |

This foundation is obtained in the form of a water-in-oil (W/O) emulsion by mixing the fatty phase and the aqueous phase with stirring. This gives a foundation with a good consistency which is easy to apply and has a very rapid drying time.

Example 3: Waterproof Mascara

| | |
|---|---|
| Methoxynonafluorobutane | 25.0 g |
| Paraffin | 4.6 g |
| Isopar | 15.0 g |
| Carnauba wax | 9.6 g |
| Beeswax | 10.0 g |
| Propylene carbonate (plasticizer) | 3.8 g |
| Hydroxyethylcellulose (polymer thickener) | 0.6 g |
| Bentone (rheological agent) | 11.4 g |
| Pigments | 10.0 g |
| Preservatives | q.s. |
| Water | q.s. 100.0 g |

Following application to the eyelashes, this mascara dries very rapidly.

Example 4: Body Makeup Product

| | |
|---|---|
| Methoxynonafluorobutane | 40.0 g |
| Cyclomethicone (and) dimethiconol sold under the name Q2 1401 ® by the company DOW CORNING | 38.4 g |
| Parleam (oil) | 1.0 g |
| Solsperse 21000 (filler) | 0.1 g |
| Cyclomethicone sold under the name DC 245 ® by the company DOW CORNING | 20.0 g |
| Nanopigments | 6.25 g |

Example 5: Nailcare Product

An oily nailcare product is prepared by mixing the following ingredients:

| | |
|---|---|
| Methoxynonafluorobutane | 10.0 g |
| Cellulose acetobutyrate | 0.5 g |
| Isopropyl alcohol | 5.0 g |
| Propylene glycol monomethylether | 3.0 g |
| Volatile silicone oil | 10.0 g |
| Vegetable oil | 64.5 g |
| Active substance (D-panthenol) | 1.0 g |
| Dyes | |
| Pyrogenic silica | 1.0 g |
| Mineral oil | q.s. 100.0 g |

This nailcare product is easy to apply and penetrates by massage into the matrix of the nail and into the nail bed; its rate of drying is very rapid.

In this example, the methoxynonafluorobutane can be replaced advantageously by an equivalent amount of ethoxynonafluorobutane or 4-trifluoromethyloctafluoromorpholine.

What is claimed is:

1. A process for accelerating the drying time of an anhydrous cosmetic make-up, sun-protection or nail care composition which consists of introducing, into said composition, a sufficient amount, for enabling a rapid drying, of at least one volatile organic solvent selected from the group consisting of a fluoroalkyl and heterofluoroalkyl compound having the following formula:

$$CH_3-(CH_2)_n-[Z]_t-X-CF_3$$

in which:

X is linear or branched divalent perfluoroalkyl radical having 2 to 5 carbon atoms, Z represents O, S or NR where R is hydrogen or a radical $-(CH_2)_n-CH_3$ or $-(CF_2)_m-CF_3$, where m is 2, 3, 4 or 5, n is 0, 1, 2, or 3 and t is 0 or 1, the said volatile organic solvent having a vapor pressure of more than 20 m bar (2000 Pa) at 25° C. and a boiling point between 20° C. and 75° C.

2. The process according to claim 1, wherein the heterofluoroalkyl compound is methoxynonafluorobutane or ethoxynonafluorobutane.

3. The process according to claim 1, wherein the volatile solvent is present in the composition in a proportion of between 2 and 98% by weight relative to the total weight of the composition.

4. The process according to claim 1, wherein the cosmetic composition is anhydrous and is in the form of a mascara, eyeliner, lipstick, eyeshadow or rouge or of a nailcare product.

5. The process, according to claim 1, wherein the composition further comprises particles of a substance selected from the group consisting of a pigment, a dye, a filler and mixture thereof.

6. The process according to claim 5, wherein the proportion of filler in the composition is no more than 98% by weight relative to the total weight of the composition.

7. The process, according to claim 5, wherein the proportion of the particles in the composition is between 0.1 and 15% by weight, relative to the total weight of the composition.

* * * * *